(12) United States Patent
Rovegno (10) Patent No.: US 6,315,712 B1
(45) Date of Patent: Nov. 13, 2001

(54) VIDEO ENDOSCOPIC PROBE WITH A DISTAL COLOR CCD SENSOR

(75) Inventor: Jean Rovegno, La Ciotat (FR)

(73) Assignee: Tokendo (Sarl), La Ciotat (FR)

( * ) Notice: Subject to any disclaimer, the term of this patent is extended or adjusted under 35 U.S.C. 154(b) by 0 days.

(21) Appl. No.: 09/426,749

(22) Filed: Oct. 26, 1999

(30) Foreign Application Priority Data

Oct. 27, 1998 (FR) .................................................. 98 13708

(51) Int. Cl.$^7$ ................................ A61B 1/05; A61B 1/07

(52) U.S. Cl. ......................... 600/109; 600/131; 600/110; 600/132; 600/182

(58) Field of Search ..................................... 600/109, 110, 600/112, 118, 131, 132, 160, 182, 130; 348/65, 71, 76

(56) References Cited

U.S. PATENT DOCUMENTS

| | | |
|---|---|---|
| D. 358,471 | 5/1995 | Cope et al. . |
| 4,537,453 | 8/1985 | Takeuchi . |
| 4,539,586 | 9/1985 | Danna et al. . |
| 4,706,118 | 11/1987 | Kato et al. . |

(List continued on next page.)

FOREIGN PATENT DOCUMENTS

| | | |
|---|---|---|
| 0131971 | 1/1985 | (EP) . |
| 0218226 | 4/1987 | (EP) . |
| 587512 | 3/1994 | (EP) . |
| 587514 | 3/1994 | (EP) . |
| 730844 | 9/1996 | (EP) . |
| 97/15144 | 4/1997 | (WO) . |
| 97/41767 | 11/1997 | (WO) . |

OTHER PUBLICATIONS

Patent Abstract of EP 0587514.
Patent Abstract of EP 0587512.
Patent Abstract of EP 0730844.
Patent abstracts of Japan for JP 62–054215.

*Primary Examiner*—John P. Leubecker
(74) *Attorney, Agent, or Firm*—Greenblum & Bernstein, P.L.C.

(57) ABSTRACT

A video endoscopic probe has a distal terminal utilizing an objective, a color CCD sensor, and an electrical interface microcircuit. The probe utilizes a continuous bundle of optical fibers which is coupled to a light source. The probe also has a video processor coupled to an electrical interface microcircuit. This video processor is adapted to supply and synchronize electrical signals from the color CCD sensor, to process the electrical signal generated by said color CCD sensor, and to produce a video signal. The color video monitor is adapted to receive the video signal produced by the video processor. The probe also has a tubular probe coupled to the distal terminal and a control handle adapted to include the video processor and the color video monitor. A multiconductor electrical is used to couple the video processor to the electrical interface microcircuit. A regulated power supply is also used and is adapted to deliver stabilized direct current voltages for operating the video processor, video monitor, electrical interface microcircuit, and said color CCD sensor. An electrical cable is coupled to the video processor and is adapted to supply a direct current electrical voltage to said power supply. The power supply is adapted to output a direct current supply voltage through the electrical cable which is variable around a nominal value. A cylindrical piece is fixedly coupled to the control handle. The control handle is a hand-held handle having one end arranged to fixedly surround a cylindrical piece and the other end has an interface coupling. The cylindrical piece has a first longitudinal opening, adapted to pass the bundle of optical fibers, and a second longitudinal opening adapted to pass the electrical cable.

22 Claims, 2 Drawing Sheets

U.S. PATENT DOCUMENTS

| | | |
|---|---|---|
| 4,831,444 | 5/1989 | Kato . |
| 4,931,867 | 6/1990 | Kikuchi . |
| 5,373,317 | 12/1994 | Salvati et al. . |
| 5,434,615 | 7/1995 | Matumoto . |
| 5,441,043 | 8/1995 | Wood et al. . |
| 5,585,840 | 12/1996 | Watanabe et al. . |
| 5,701,155 | 12/1997 | Wood et al. . |
| 5,785,644 * | 7/1998 | Grabover et al. .................... 600/109 |
| 5,873,814 * | 2/1999 | Adair ................................... 600/109 |
| 5,879,289 * | 3/1999 | Yarush et al. ....................... 600/109 |
| 5,986,693 * | 11/1999 | Adair et al. ......................... 600/109 |

\* cited by examiner

VIDEO ENDOSCOPIC PROBE WITH A DISTAL COLOR CCD SENSOR

CROSS-REFERENCE TO RELATED APPLICATIONS

The present application claims priority under 35 U.S.C. § 119 of French Patent Application No. 98/13708, filed on Oct. 27, 1998, the disclosure of which is expressly incorporated by reference herein in its entirety.

BACKGROUND OF THE INVENTION

1. Field of the Invention

The invention concerns a video endoscopic probe with a distal color CCD sensor. The technical field of the invention is that of endoscopy devices.

The term "video endoscopy" designates an examination which allows one to obtain on a television monitor the image of a target situated inside of a dark cavity into which the distal end of a video endoscopic probe has been introduced.

2. Discussion of Background Information

Among the known devices pertaining to color video endoscopy, it is possible to distinguish two types of video endoscopes. The first type covers devices in which the image of the target observed inside of a cavity is transmitted by an endoscope or a fibroscope to a color CCD sensor situated outside of the cavity. This first type of video endoscope corresponds in particular to cameras are color CCD sensor equipped with a focussing objective and a mechanical connection device allowing the objective of said camera to be locked on the cup surrounding the eyepiece of an endoscope or fibroscope, this camera is connected by an umbilical cable to an external video processor which generates a video signal which signal can be viewed directly on a color monitor.

The second type of video endoscope covers devices in which the CCD sensor is housed directly in the distal end of the video endoscopic probe. The sensor is therefore introduced inside of the cavity in which the target to be examined is situated. Among the devices arising from this second type of embodiment, it is possible to distinguish two categories of video endoscopes with a distal CCD sensor capable of delivering color video images.

The first category covers devices in which the CCD sensor is a "monochromic" sensor (also called "black and white" sensor) which delivers an electrical signal containing only the luminance information. In this case, obtaining a video signal which can be viewed on a color monitor requires an illumination device which can sequentially deliver flashes corresponding to the three primary colors, a device for picking up the video signals generated sequentially by the monochromic distal CCD sensor during the flashes, and a processor which makes it possible to continually store the last three monochromic video frames in memory and to reconstitute a video signal which can be utilized directly on a color monitor from the three monochromic frames available in memory.

The second category of video endoscopes with distal CCD sensor covers devices in which the CCD sensor is a "trichromic sensor" (also called "color" sensor) which, in association with an illumination device which delivers a permanent and continuous white light, provides an electrical signal containing the luminance and chrominance information. This signal is transmitted to a processor which generates a video signal which can be directly viewed on a color monitor.

The difficulties in designing a video endoscope with a distal CCD sensor result essentially from the diversity of the applications requiring a range of probes whose useful lengths can range between 20 cm (for a dental probe) and 50 m (for a tubing inspection probe), and therefore from the need to adapt the characteristics of the video processor, as a function of the length of the electrical cable connecting the processor to the distal CCD sensor.

The joint functioning of a color CCD sensor, and of the video processor with which it is associated, in effect proceeds essentially from correct management of the phase shifts of the different high-speed clocks (14.2 MHZ in standard PAL) which are generated by the processor and described hereinafter.

"Pixel" clocks—This relates to clocks transmitted to the distal CCD sensor, in which they are used, on the one hand, for synchronizing the reading of the electrical voltages contained in the unit cells (called pixels) of the light-sensitive layer of the sensor and, on the other hand, for extracting from these unit voltages the significant information which, after integration, will constitute the electrical signal delivered by the CCD sensor and transmitted to the video processor.

"Sampling" clock—This relates to a clock used locally for synchronizing the sampling by the video processor of the electrical signal generated by the CCD sensor and transmitted to the processor. The proper functioning of the processor necessarily requires that the sampling clock be completely in phase with the incident electrical signal. Given the length of the electrical connections connecting the sensor to the video processor with which it is associated, misalignment of the color CCD sensor in the distal end of the video endoscopic probe introduces a redhibitory phase shift at the level of the processor between the sampling clock and the incident electrical signal. A phase shift results from the running total of the transmission delay to the CCD sensor of the pixel clocks generated by the video processor and the transmission delay to the video processor of the electrical signal generated by the CCD sensor. The method of remedying such a dysfunction consists of delaying either the sampling clock or the pixel clocks transmitted to the distal CCD sensor by the video processor, and in this way compensating for the overall phase shift mentioned above. The modalities of implementation of one or the other of these delay devices, and the connection problems proceeding from them, vary as a function of the integration mode of the video processor which can, depending on the architecture used, be external to the video endoscopic probe with distal CCD sensor or an integral part of the probe.

The video endoscopes arising from the first type of architecture utilize a case generally combining a light generator and a video processor. It is this case on which the connection device connected with the proximal end of the umbilical cable of the video endoscopic probes with distal CCD sensor is connected. The interchangeability of the different probe models which can be connected to the same processor obviously assumes a complete compatibility between the processor and the probes, and therefore integration in each probe of a specific delay device.

For example, the video endoscopic probes with distal monochromic CCD sensor described in U.S. Pat. No. 4,539, 586 (Welch Allyn, September 1985) are equipped with a connection box allowing the probes to be connected on the case merging a generator of trichromic flashes and a video processor. This connection box contains two devices allowing adjustment of the characteristics of the two pixel clocks provided by the video processor and transmitted to the distal monochromic CCD sensor. An amplifier allows for adjustment of the level of the electrical signal generated by the distal monochromic CCD sensor, and transmitted to the video processor.

European Patent 0 218 226 B1 (Olympus, October 1986) describes a video processor which has a synchronization generator capable of delivering several sampling clock types corresponding to the number of endoscopic probe models having a distal CCD sensor, the connectors of the probes contain an electronic key which, when suitably decoded by the processor, allows the processor to select automatically the sampling clock suited to the connected probe.

U.S. Pat. No. 5,434,615 (Fuji Optical, July 1995) describes a video endoscopic probe with distal color CCD sensor having a control handle in which is housed the sampler, normally associated with the video processor, and an umbilical cable whose proximal end is equipped with a connection box in which the sampling clock generator is housed. The clock has a delay which is suited to the characteristics of the probe in consideration. The probe is connected to an external video processor which directly receives the electrical signal delivered by the sampler housed in the control handle of the probe. The probe utilizes synchronizing by the sampling clock generator which housed in the connector of the probe.

Outside of the particular configurations described in the patents mentioned above, the video endoscopic probes which can be connected on an external video processor most often have a delay device integrated in the connector or in the handle of said probe and which acts on the pixel clocks generated by the video processor and transmitted to the distal color CCD sensor. In any case, the main technical disadvantage inherent to this first type of architecture lies in the break of continuity introduced by the connection of the probe, of the electrical connection (conductors and braided ground strap) bringing to the video processor the electrical signal generated by the distal color CCD sensor, electrical signal whose transport proves to be delicate because of its low level as well as its wide pass band. It is also appropriate to note that, even if this type of architecture allows for delaying the pixel clock signals transmitted by a video processor to a distal color CCD sensor in such a way as to make video endoscopic probes of different lengths compatible with the same processor, it does not, for all that, make corrections which would allow compensation for the statistical dispersion of the characteristics of the color CCD sensors implemented in the probes.

The disadvantages mentioned above have been eliminated in the video endoscopes arising from the second type of architecture mentioned above, and in which each video endoscopic probe with distal color CCD sensor has its own video processor, these probes being connected to an external case merging a light fixture and having a device which delivers the various voltages for the electrical supply of the video processor. It is thus possible under these conditions for each processor to be completely adjusted as a function of the length of the probe in which it is integrated (adjustment of the delay of the sampling clock or of the delay of the pixel clocks), as well as a function of the specific characteristics of the distal CCD sensor with which it is associated (adjustments of colorimetry allowing to correct the dispersion of the parameters of the CCD sensor).

Thus, U.S. Pat. Nos. 5,701,155 (Welch Allyn, December 1997) and 5,441,043 (Welch Allyn, September 1992), and European Patents 0 587 514 A1 (Welch Allyn, September 1993) and 0 587 512 A2 (Welch Allyn, September 1993) describe video endoscopic probes having a distal color CCD sensor which is equipped with a connection box connected with the proximal end of the umbilical cable of the probes and which is used as housing for a video processor. The box is equipped with a composite connector which is connected on an external box combining a light fixture, the electrical supply for the video processor integrated in the connection box, and allows the case to be connected to a color video monitor. The main drawback inherent to the concept described in these patents results from the need to connect the video endoscopic probe with distal color CCD sensor, to a specific external case in which a light fixture in particular is housed, on whose color temperature is fixedly set the device for the white balance adjustment of the video processors integrated in the probe connectors. This solution prohibits the user from choosing the light source which is implemented.

In any case, the connection device connected with the proximal end of the umbilical cable of a video endoscopic probe with distal CCD sensor must, under these conditions, simultaneously ensure the continuity of a certain number of electrical connections and the transmission to a bundle of optical fibers of the light emitted by a light fixture. The connection of video endoscopic probes which can be connected on a single case (merging light fixture and electrical supply devices, or light fixture and video processor) will generally have a "composite" structure different from the "Y-shaped" structure of the connection devices of probes which can be connected on two distinct cases (for example, a light generator and a video processor).

The six patents mentioned hereinafter relate to connection devices allowing to connect video endoscopic probes with distal CCD sensor to a single external case.

European Patent EP 0 131 971 B1 (Olympus, July 1984) describes a fibroscope connection device capable of ensuring simultaneously the continuity of a light connection and of several electrical connections. This device could therefore be easily adapted to a video endoscopic probe with distal CCD sensor. The device is made up of a cylindrically shaped connector with an axial fibered terminal and several lateral electrical connection pins distributed in an annular manner around the end of said connector.

U.S. Pat. No. 4,539,586 (Welch Allyn, September 1985) describes a box integral with the proximal end of the umbilical cable of a video endoscopic probe with a distal monochromic CCD sensor and utilizes an integrated electronic board which is adapted to ensuring the interchangeability of the probes. The proximal side of the box has a series of connectors allowing it to connect simultaneously a light connection and several connections of electrical or pneumatic nature. The particularity of this patent lies in the fact that it describes simultaneously the principle of a composite connector and the integration of an electronic circuit in said connector, a concept which has been used again in U.S. Pat. Nos. 5,701,155 (Welch Allyn, December 1997) and 5,441,043 (Welch Allyn, September 1992), and European Patents 0 587 512 A2 (Welch Allyn, September 1993) and 0 587 514 A1 (Welch Allyn, September 1993) which relate to endoscopic probes with a distal color CCD sensor equipped with a composite connection box in which a video processor is integrated. The connection mode described above has been used in particular by the company Welch Allyn (System 2000 and System XT) and by the company Pentax (System EPM 3000).

European Patent EP 0 730 844 A1 (Olympus, September 1996) describes a connection device allowing it to associate a video endoscopic probe with distal color CCD sensor with two distinct cases, and therefore all the more so with a single case. The device consists of one cylindrical connector equipped with an axial fibered terminal which is plugged directly into the connecting coupling of a light generator. This connector has a lateral multipin electrical connection coupling on which a multiconductor electrical cable is connected. The other end is plugged into the connection coupling of a video processor. The drawback of such a connection device, which is implemented by the company Olympus (System Evis 100), lies in the multiplicity of the connections affecting the electrical linkages, certain ones of which transmit electrical signals which have simultaneously a low level and a wide pass band. Other variants of connection devices allowing to associate a video endoscopic probe with distal color CCD sensor with two distinct cases have also been implemented by the company Olympus; these variants consisting either of fixedly associating a lighting connecting strap with an electrical connector, or of fixedly associating an electrical connecting strap with a lighting connector.

The use of a video endoscopic probe with distal color CCD sensor obviously assumes that the image of the target situated in front of the distal end of the probe is displayed on a color video monitor. This monitor is most often connected on the external case associated with said probe. The recent miniaturization of LCD technology video screens has enabled the consideration of the integration of a video monitor with a small space requirement in the control handle of a video endoscopic probe with a distal color CCD sensor. A color video monitor integrated in the control handle can be used for purposes other than the simple display of the video image delivered by the video endoscopic probe with distal color CCD sensor. For example; U.S. Pat. No. 5,373,317 (Welch Allyn, December 1994) describes a video endoscopic probe with a distal color CCD sensor whose control handle has a color video monitor and a control joystick. The joystick can be used either for controlling an electrical motorization system integrated in the handle and adapted for modifying the orientation of the distal articulated prop of the probe, or for moving indexes in the image displayed by the video monitor. This allows for the managing of a program for processing the image displayed on the monitor. The aesthetic appearance of such a control handle having an integrated video monitor and a joystick for control of the prop is described in the U.S. Pat. No. DES.358471 (Welch Allyn, May 1995). These two patents mentioned above have been implemented in the video endoscopic probes of the System XT developed by Welch Allyn, probes whose electronic structure corresponds to European Patent 0 587 514 A1 (Welch Allyn, September 1993). In any case, the integration of a color video monitor in the control handle of a video endoscopic probe with distal color CCD sensor assumes under these conditions the integration, in the umbilical cable integral with said handle, of additional electrical connections between the video processor and the handle, connections which are adapted for providing the monitor with the video signal and the supply voltages necessary for its functioning.

SUMMARY OF THE INVENTION

The present invention arises from the previously discussed second category of video endoscopes with distal color CCD sensor, i.e., video endoscopes whose architecture results from the association of the elements described hereinafter. As such the invention utilizes:

A terminal in which is housed an imaging device comprising a distal objective, a color CCD sensor on the photoelectric substrate from which the real image of the target observed by the objective is formed, and an interface microcircuit adapted for correcting the electrical signals received or generated by the CCD sensor.

A flexible or rigid inspection tube, which may or may not have an articulated distal prop, and whose distal end is associated with the terminal in which the imaging device is housed.

A control handle whose distal end is connected with the proximal end of the inspection tube.

An umbilical cable whose distal end is connected with the control handle and whose proximal end is made up of a connection device allowing the video endoscopic probe to be connected to the external electrical devices and light generator necessary for its implementation.

An illumination device made up of a bundle of non-ordered optical fibers whose distal end, housed in the distal side of the distal terminal, illuminates the observed target when its proximal end, housed in the connection device of the umbilical cable, is connected to a light generator.

A video processor which ensures the synchronization and electrical supply of the distal imaging device, processes the electrical signal generated by the imaging device, and delivers a video signal which can be viewed directly on a color monitor.

A color video monitor which displays the image of the target observed by the distal imaging device.

A light source whose color temperature corresponds to the adjustment of the white balance device integrated in the video processor, and this source has a lighting coupling in which the connection device connected with the proximal end of the umbilical cable of the probe is connected.

The present invention describes a video endoscopic probe with distal color CCD sensor integrating its own method of processing and displaying the video signal and whose implementation is completely automated and only requires the connection to the probe of a commonplace light generator and of an also commonplace electrical energy source.

The present invention also describes an even more autonomous version of a video endoscopic probe with a distal color CCD sensor integrating, moreover, its own lighting and whose implementation would, under these conditions, require no more than a simple connection to a commonplace electrical energy source.

The basic version of the video endoscopic probe with distal color CCD sensor constituting the present invention represents the combination of the following elements.

(A) A distal terminal in which an imaging device is fixedly housed, having a distal objective which forms a real image of the observed target on the light-sensitive layer of a color CCD sensor with which it is associated, the proximal side of the color CCD sensor being fixedly integral with an interface microcircuit which is adapted for correcting the electric signals received or generated by the color CCD sensor.

(B) A flexible or rigid inspection tube, which may or may not have an articulated distal prop, and whose distal end is fixedly associated with the distal terminal according to (B).

(C) A control handle whose distal end is fixedly integral with the proximal end of the inspection tube according to (B). The handle possibly including some mechanical methods necessary for controlling the orientation of the articulated distal prop of the inspection tube according to (B).

(D) A parallelepiped-shaped box mechanically connected with the proximal end of the control handle according to (C).

(E) A tubular handle whose distal end is mechanically connected with the lower part of the proximal end of the control handle according (C).

(F) A flexible umbilical cable whose distal end is fixedly integral with the proximal end of the tubular handle according to (E).

(G) A cylindrical connection device, devoid of any electrical adapting device, whose distal end is fixedly integral with the proximal end of the umbilical cable according to (F), and whose proximal side has an axial cylindrical terminal allowing the umbilical cable according to (F) to be connected to the connection coupling of a commonplace external light generator. The connection device is also equipped with a lateral electrical connection coupling adapted for the connection of a commonplace external electrical energy source which delivers a direct current voltage with a value equal, for example, to 12 Volts and constituting the sole electrical supply of the video endoscopic probe with distal color CCD sensor.

(H) An illumination device made up of a continuous bundle of non-ordered optical fibers running successively without break of continuity through the inspection tube according to (B), through the control handle according to (C), through the tubular handle according to (E), and then through the umbilical cable according to (F). The distal end of said bundle of fibers is suitably spread around the imaging device housed in the distal terminal according to (A), and illuminates the observed target when its proximal end, fixedly housed in the axial cylindrical terminal arranged on the proximal side of the connection device according to (G), is connected to a light generator.

(I) A video processor housed in the distal part of the box according to (D) and connected to the imaging device housed in the distal terminal according to (A) by a multi-conductor electrical cable running without break of continuity through the control handle according to (C) and then through the inspection probe according to (B). The phase shift of the pixel clock generated by the video processor and transmitted by this connecting cable to the distal imaging device (or, another solution, the phase shift of the high-speed clock which synchronizes the sampling by the video processor of the incident electric signal generated by the distal color CCD sensor) is fixedly set continually by way of delay lines as a function of the length of the connecting cable. The processing by the video processor of the electrical signal generated by the distal color CCD sensor and transmitted by this connecting cable can be furthermore completely, continually adapted to the specific characteristics of the distal color CCD sensor. The regulation of the level of sensitivity of the video processor according to an automatic control mode acting simultaneously on the device for automatic gain control (AGC) and on the opening of the electronic diaphragm of the color CCD sensor (shutter), allows for the compensating automatically, of great variations of the lighting level of the target, and therefore frees up the user from any concern with any adjustment of the sensitivity of the video processor and/or of the intensity of the lighting delivered by the light generator. The organization described above therefore makes it possible to continually optimize the functioning of the video processor as a function of the length of the inspection probe, the specific characteristics of the distal color CCD sensor, and the lighting level of the target observed. This organization moreover is particularly favorable for the electrical insulation of the connections connecting, without break of continuity, the imaging device housed in the distal terminal according to (A) to the video processor. The video processor has a power supply which delivers the various regulated direct current voltages, which are necessary for its functioning, as well as for that of the video monitor according to (J), and of the imaging device housed in the distal terminal according to (A). The power supply is itself supplied by a direct current electrical voltage delivered by the distal end of an electrical cable running without break of continuity through the control handle according to (C), through the tubular handle according to (E) and then through the umbilical cable according to (F), and whose proximal end is supplied by the electrical connection coupling of the connection device according to (G). The arrangements confirm the advantages offered in the matter of functioning autonomy by the video endoscopic probe with a distal color CCD sensor which is the subject of the present invention.

(J) A flat color video monitor, for example, with LCD technology, housed in the proximal part of the box according to (D), directly receives the video signal produced by the video processor according to (I) housed in the same box and therefore displays the image of the target observed by the imaging device housed in the distal terminal according to (A). The integration of a light-weight color video monitor in the control handle according to (C) of the video endoscopic probe with a distal color CCD sensor constituting the present invention allows for avoiding the use of an external video monitor and therefore reinforces the advantages offered by the video endoscopic probe in the matter of functioning autonomy.

(K) A panel of sensitive keys integrated on the proximal side of the box according to (D) and associated with the digital microcontroller which ensures that the management of the video processor according to (I) allows the operator to modify the functioning parameters of the video processor. This panel of keys in particular has an "AUTO LOCK" key allowing for automatically locking the device for adjusting the white balance of the video processor as a function of the chromatic characteristics of the video image of the target observed by the distal terminal according to (A) and illuminated by the distal end of the bundle of optical fibers of the illumination device according to (H). The arrangements make it possible to free the operator from ? the color temperature of the light generator connected to the video endoscopic probe and therefore to use any commonly used generator model.

A more sophisticated version of the video endoscopic probe with a distal color CCD sensor constituting the present invention proceeds from the specific arrangements described hereinafter.

Removal of the umbilical cable according to (F) and of the connection device according to (G).

Integration, in the distal end of the tubular handle according to (E) of the proximal end of the bundle of optical fibers, of the illumination device of the video endoscopic probe.

Integration in the tubular handle according to (E) of a light fixture having a reflector which concentrates the light radiation emitted by the light on the proximal end of the bundle of optical fibers of the illumination device.

Integration in the tubular handle according to (E) of an electronic device for the electrical supply of the light fixture, the device being supplied by direct current voltage with a value identical to the supply voltage of the video processor according to (I).

Integration in the proximal end of the tubular handle (E) of a multipin electrical connection coupling adapted to being connected on the supply source of the video endoscopic probe.

Accordingly, the present invention is directed to a video endoscopic probe that includes a distal terminal having an objective, a color CCD sensor, and an electrical interface microcircuit, a continuous bundle of optical fibers having a proximal end coupled to a light source and a distal end located in the distal terminal, and a video processor coupled to the electrical interface microcircuit. The video processor is adapted to supply and synchronize electrical signals from the color CCD sensor, to process the electrical signal generated by the color CCD sensor, and to produce a video signal. A color video monitor is adapted to receive the video signal produced by the video processor, a tubular probe is coupled to the distal terminal, and a control handle is adapted to include the video processor and the color video monitor. The tubular probe includes a proximal end coupled to the control handle. A multiconductor electrical cable couples the video processor to the electrical interface microcircuit, and a regulated power supply is adapted to deliver stabilized direct current voltages for operating at least the video processor, the video monitor, the electrical interface microcircuit, and the color CCD sensor. An electrical cable coupled to the video processor is adapted to supply a direct current electrical voltage to the power supply. The power supply is adapted to output a direct current supply voltage through the electrical cable which is variable around a nominal value. A cylindrical piece is fixedly coupled to a proximal lower part of the control handle, the control handle includes a hand-held handle having a distal end arranged to fixedly surround the cylindrical piece and a proximal end including an interface coupling, and the cylindrical piece includes a first longitudinal opening adapted to pass the bundle of optical fibers, and a second longitudinal opening adapted to pass the electrical cable.

In accordance with the features of the instant invention, the continuous bundle of optical fibers can be adapted to illuminate a target, the video processor and the color video monitor can be integrated in the control handle, the color video monitor can directly receive the video signal from the video processor, the hand-held handle can include a cylindrical tubular hand-held handle, and the nominal voltage may be 12 volts and the direct supply voltage may vary between approximately 9 and 16 volts.

According to another feature of the present invention, an umbilical cable can have a distal end coupled to the proximal end of the hand-held handle and can have a proximal end coupled to a connection device. The connection device may include an axial terminal in which the proximal end of the bundle of optical fibers are located. The bundle of fibers may be adapted to couple the connection device to the distal terminal, and the axial terminal may be plugable into an external light generator. Further, the connection device may include a lateral electrical connection coupling that is electrically coupled to a proximal end of the electrical cable, which can be adapted to couple the connection device to the video processor, and the lateral electrical connection coupling may be connectable to an external electrical source. Further, the umbilical cable can be a tubular umbilical cable, a distal end of the connection device, to which the proximal end of the umbilical cable is coupled, may not include an internal electrical adaptation device, the bundle of optical fibers can run directly and without a break of continuity through the umbilical cable, the hand-held handle, the first longitudinal opening, the control handle, and the tubular probe, and the electrical cable can run directly and without a break of continuity through the umbilical cable, the hand-held handle, the second longitudinal opening, and the control handle.

According to still another feature of the invention, a multiconductor cable can include a coaxial cable that may be coupled to the video processor and may be adapted to receive the video signal. The connection device can further include a lateral coaxial connection coupling that can be electrically coupled to the coaxial cable, which can adapted to couple the connection device to the video processor. The lateral coaxial connection coupling may be connectable to an external video monitor. Further, the multiconductor cable may be adapted to run successively through the umbilical cable, the hand-held handle, the second longitudinal opening, and the control handle.

In accordance with a further feature of the invention, a digital microcontroller can have an RS 232T interface, and the digital microcontroller can be adapted to control operation of the video processor. The multiconductor cable may include a plurality of conductors coupled to an RS 232T coupling, such that the RS 232T coupling can be coupled to the RS 232T interface. The connection device may further include a lateral multipin connection coupling which is electrically coupled to the RS 232T link, such that the RS 232T link may be adapted to couple the connection device to the video processor. The lateral multipin connection coupling can be couplable to the RS 232T interface, whereby the RS 232T interface can be couplable to the RS 232T link. Further, the multiconductor cable is adapted to run successively through the umbilical cable, the hand-held handle, the second longitudinal opening, and the control handle.

According to a still further feature of the present invention, the proximal end of the bundle of optical fibers may be mounted within the first longitudinal opening, and the video endoscopic probe can further include a light fixture located within the hand-held handle that can include a reflector adapted to concentrate light radiation emitted by the light source onto the proximal end of the bundle of optical fibers. The light fixture may be adapted to receive a stabilized voltage from a regulated light fixture power supply, such that the regulated power supply can be located within the hand-held handle, and such that the power supply voltage to the light fixture can be the same as that to the video processor. The interface coupling can include a multipin electrical connection coupling that is electrically connected to an internal electrical cable forming a first branch circuit to supply electrical power to the regulated light fixture power supply and a second branch circuit to supply electrical power to the regulated power supply, such that the second branch circuit is adapted to run successively through the hand-held handle, the second longitudinal opening, and the control handle. Further, an internal multiconductor cable can be provided. The multipin electrical connection coupling can be adapted to be electrically coupled to the internal multiconductor electrical cable, and the multipin electrical connection including an RS 232T link. The internal multiconductor cable can be arranged to couple the multipin electrical connection coupling to the video processor, such that the internal multiconductor cable can be adapted to at least one of transmit the video signal generated by the video processor and couple the RS 232T link to the video processor. Further still, the internal multiconductor cable can be adapted to run successively through the hand-held handle, the second longitudinal opening, and the control handle. The proximal end of the bundle of optical fibers may be polished to receive the light radiation.

In accordance with another feature of the instant invention, a digital microcontroller can be coupled to a panel of operating keys, such that the digital controller is adapted to control the video processor. A device for adjusting white balance of the video processor as a function of chromatic characteristics of a video image of the target, which is illuminated by the bundle of optical fibers, can be provided. The panel of operating keys can include a special key adapted to automatically lock the white balance adjustment device. Further, the panel of operating keys can be located on the control handle.

According to still another feature of the invention, a sensitivity of the video processor can be regulatable as a function of a lighting level of the target through an automatic control mode that simultaneously considers a gain of the video processor and an opening of an electronic diaphragm of the distal color CCD sensor, which automatically compensates for great variations in lighting level occurs.

In accordance with another feature of the invention, a phase shift device can be adapted to compensate for transmission delays of the electrical signals traveling through the multiconductor electrical cable. The phase shift device may include a delay line acting on a pixel clock generated by the video processor and transmitted to the electrical interface circuit. Further, the phase shift device can further include a delay line acting on a clock which synchronizes sampling by the video processor of an incident electrical signal generated by the distal color CCD sensor and transmitted by the multiconductor cable.

According to yet another feature of the present invention, a prop device can be coupled to the tubular probe and to the distal terminal. The prop device may include a series of rings, such that each ring is articulated with its adjacent rings to enable the prop device to be oriented in two perpendicular planes. Two flexible cables, which extend through the tubular probe, can be adapted to control translational movements of the prop device in the two perpendicular planes. An actuator located within the control handle may be coupled to the two flexible cables and may be adapted to drive the two flexible cables in respective ones of the two perpendicular planes. Further, the actuator can include two mechanical actuators, and each of the two mechanical actuators may be coupled to an external control wheel. Alternatively, the actuator comprises two motorized actuators. Moreover, a joystick can be adapted to control a starting and rotational direction of the two motorized actuators, such that the joystick can be coupled to the control handle and can be adapted for movement with four degrees of freedom. Further, power supply voltages for the two motorized actuators can be the same as the power supply voltage of the video processor.

The present invention is also directed to a video endoscopic probe including a distal terminal including an objective, a color CCD sensor, and an electrical interface microcircuit, a continuous bundle of optical fibers coupled to a light source and to the distal terminal, a video processor coupled to the electrical interface microcircuit, and a color video monitor adapted to receive the video signal produced by the video processor. A tubular probe is coupled to the distal terminal, a control handle is adapted to include the video processor and the color video monitor, and the tubular probe is coupled to the control handle. A multiconductor electrical cable couples the video processor to the electrical interface microcircuit and a regulated power supply is adapted to deliver stabilized direct current voltages for operating at least the video processor, the video monitor, the electrical interface microcircuit, and the color CCD sensor. An electrical cable coupled to the video processor is adapted to supply a direct current electrical voltage to the power supply, such that the power supply is adapted to output a direct current supply voltage through the electrical cable which is variable around a nominal value. A cylindrical piece is fixedly coupled a lower part of the control handle, the control handle includes a hand-held handle having a portion arranged to fixedly surround the cylindrical piece and further having an interface coupling, and the cylindrical piece includes a first longitudinal opening adapted to pass the bundle of optical fibers, and a second longitudinal opening adapted to pass the electrical cable.

BRIEF DESCRIPTION OF THE DRAWINGS

The present invention is further described in the detailed description which follows, in reference to the noted plurality of drawings by way of non-limiting examples of embodiments of the present invention, in which like reference numerals represent similar parts throughout the several views of the drawings, and wherein.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
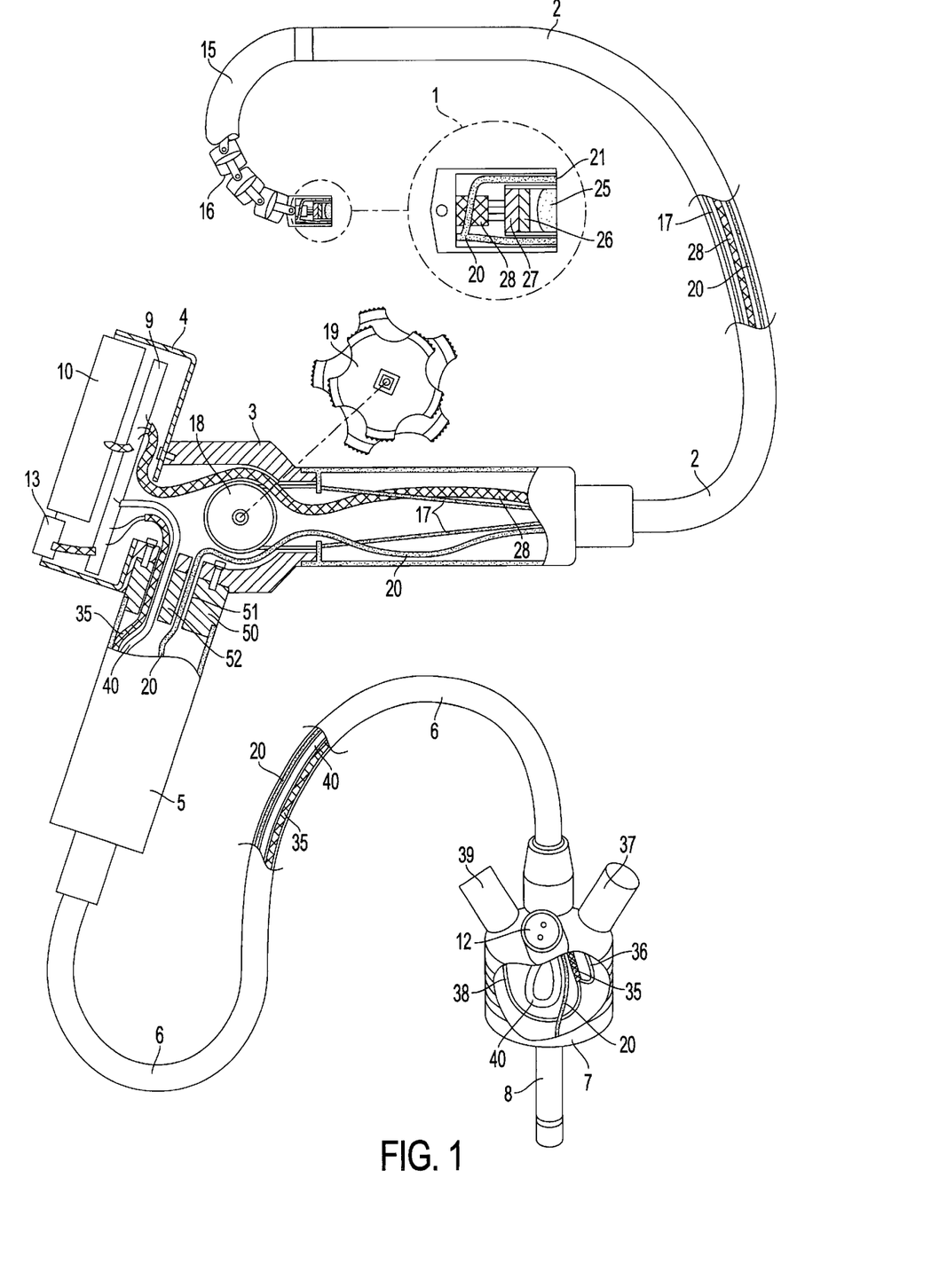
FIG. 1 illustrates the functional organization of the basic version of the video endoscopic probe with a distal color CCD sensor.

FIG. I diagrammatically illustrates the functional organization of the basic version of the video endoscopic probe with a distal color CCD sensor. There is provided the following:

A distal terminal 1, fixedly associated with the distal end of an articulated prop 15, contains an imaging device comprising an objective 25, a color CCD sensor 26 and an interface microcircuit 27 adapted to correct the electrical signals received or generated by the CCD sensor. The microcircuit ensures the filtering of the supply voltages of the CCD sensor, the shaping of the high-speed clocks for the synchronization of the sensor, and the adaptation of the impedance of the electrical signal generated by the sensor.

The prop 15, whose proximal end is fixedly integral with the distal end of a flexible inspection tube 2, also has a series of rings 16. Each ring is articulated with respect to adjacent rings, in such a way that the distal end of said prop can be oriented in two perpendicular planes. The proximal end of the inspection tube is fixedly integral with the distal end of a control handle 3.

The orientation of the prop 15 is controlled by two pairs of cables 17 running through the flexible inspection tube 2. Two mechanical actuators 18 are housed in the central part of the control handle 3. One pair of cables actuates the orientation of the prop in one plane, and the other pair of cables actuates the orientation of said prop in a plane perpendicular to the preceding one. Two concentric wheels 19, situated on the outside of the handle 3 and whose axes are fixedly and mechanically associated with the actuators 18, allow the user to control the orientation of the prop.

The proximal end of control handle 3 is fixedly integral with the distal face of a box 4. The box is used as a housing for a video processor 9 housed within its distal part, and for a flat video color monitor 10 which is housed in its proximal part. The functioning parameters of the video processor 9 are adjusted by a panel of sensitive keys 13 situated on the proximal face of the box.

The lower part of the proximal end of the control handle 3 is fixedly integral with a cylindrical piece 50 which has two longitudinal openings 51 and 52 used respectively as passages for a bundle of illuminating fibers 20, and for the multiconductor electrical cables 35 and 40 connecting the control handle to the connection devices of the video endoscopic probe.

The cylindrical piece 50 is used as a support for the distal end of a cylindrical tubular handle 5, and it has a proximal end which is fixedly integral with the distal end of an umbilical cable 6. The proximal end of the umbilical cable 6 is fixedly integral with the connection device 7. The proximal end of the connection device has an axial cylindrical terminal 8 allowing it to connect the video endoscopic probe to a commonplace external light generator. The connection device also has three multipin electrical connection couplings 12, 37 and 39. For example, coupling 12 may be used to connect the video endoscopic probe to an electrical energy source. Coupling 37 may be used to connect an external color video monitor on the video endoscopic probe. Coupling 39 may be used to connect the video endoscopic probe to an RS 232T interface of an external computer.

The illumination device of the video endoscopic probe is made up of a continuous bundle of non-ordered optical fibers 20 running successively without break of continuity through the inspection tube 2, after first going through the control handle 3, and the longitudinal opening 51 of the cylindrical piece 50, and the handle 5, and the umbilical cable 6, and through the connection device 7. The distal end 21 of said bundle of fibers, is suitably spread around the objective 25 which is housed in the distal terminal 1. These fibers illuminate the observed target when this proximal end, which are fixedly housed in the cylindrical terminal 8 of the connection device 7, is connected to a light generator.

The video processor 9, housed in the box 4, is directly connected to the interface microcircuit 27 associated with the distal CCD sensor 26 by a multiconductor electrical cable 28 running successively without break of continuity from the control handle 3 and through the inspection tube 2. Traveling through the cable are the supply voltages for the CCD sensor, a slow "line" synchronization clocks for the CCD sensor (including in particular the control clock for the electronic diaphragm of the CCD sensor), a high-speed "pixel" synchronization clock for the CCD sensor and, in the opposite direction, the electrical signal generated by the CCD sensor. The video processor 9 has one delay line for allowing a phase shift to the pixel clock generated by the video processor, and transmitted to the electrical interface microcircuit 27 which is associated with the distal CCD sensor 26 (the interface microcircuit locally generating the integration clock). This is done in such a way that the clock synchronizing the sampling by the video processor of the electrical signal generated by the CCD sensor, is completely in phase with said incident electrical signal.

The video signal delivered by the video processor 9 is directly transmitted to the video input of a flat color monitor 10 arranged on the proximal face of the box 4. The video signal is also transmitted to the electrical connection coupling 37 of the connection device 7 by way of a coaxial connection 36 integrated in the multiconductor electrical cable 35 connecting the video processor to the connection device and running successively without break of continuity through to the longitudinal opening 52 of cylindrical piece 50, after going through the handle 5 and the umbilical cable 6.

The functioning of the video processor 9 is managed by a control device integrated in the video processor and comprising a digital microcontroller. It also uses a memory and an interface circuit to the standard RVS 232T. The microcontroller is associated with a panel of sensitive keys 13 situated on the proximal face of the box 4 and allowing the operator to modify the functioning parameters of the video processor. The panel in particular has a key allowing it to automatically lock in "AUTO LOCK" mode, the device for adjusting the white balance of the video processor as a function of the chromatic characteristics of the color video image of the target observed by the distal terminal 1, and illuminated by the distal end 21 of the bundle of optical fibers 20. The arrangements also allow for connecting the video endoscopic probe to a non-specific light generator. A RVS 232T interface circuit of the control device is installed in the video processor and is connected to the multipin electrical connection coupling 39 of connection device 7 by several conductors 38 integrated in the multiconductor cable 35, which connects the video processor to the connection device, and runs successively without break of continuity through the longitudinal opening 52 of the cylindrical piece 50, after going through the cylindrical handle 5 and the umbilical cable 6.

The video processor 9 has a power supply (not shown) which delivers the various regulated direct current voltages necessary for the functioning of said video processor, the video monitor 10, the distal color CCD sensor 26, and the interface microcircuit 27 associated with the CCD sensor. The power supply is itself supplied by a single direct current voltage whose value can vary greatly around its nominal value. The power supply is itself also supplied by an electrical cable 40 running through the longitudinal opening 52 of the cylindrical piece 50, the cylindrical handle 5, and through the umbilical cable 6. This cable connects without break of continuity the video processor 9 to the electrical connection coupling 12 of the connection device 7. This coupling can be connected to a commonplace electrical energy source such as, for example, a storage battery which delivers a nominal voltage of 12 Volts which can vary between 9 and 15 Volts.

Figure 2:
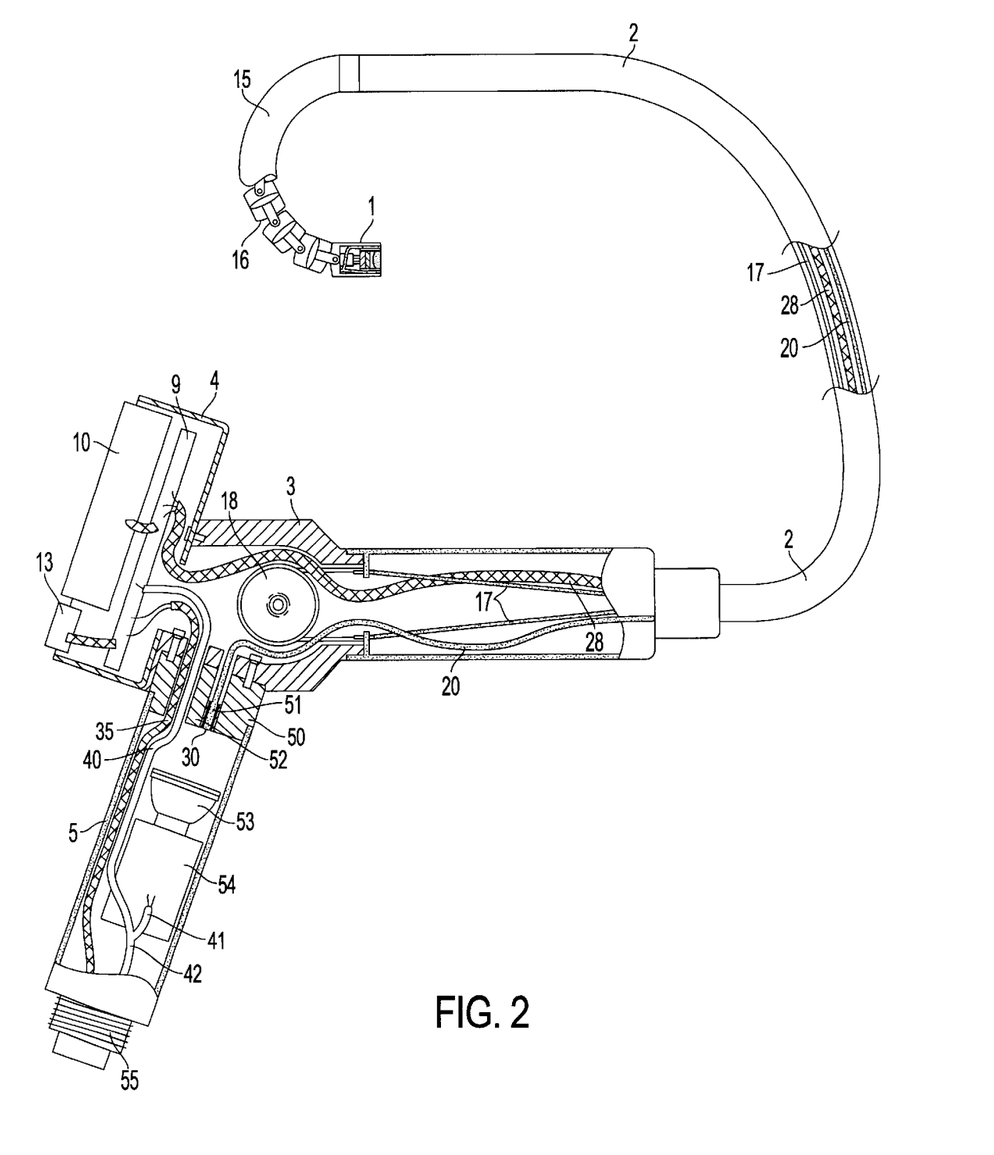
FIG. 2 illustrates the functional organization of a version with integrated lighting of the video endoscopic probe with a distal color CCD sensor.

FIG. II diagrammatically illustrates the functional organization of a version having integrated lighting of the video endoscopic probe with a distal color CCD sensor constituting the present invention.

This version is characterized by the elimination of the umbilical cable 6 as well as connection device 7, and by the integration of a lighting device in the cylindrical handle, and also by the integration, in the proximal end of said cylindrical handle, of a multipin electrical connection coupling which constitutes the sole interface of this version of the video endoscopic probe. All the other arrangements of this version furthermore remain identical to those previously described as to FIG. I.

The illumination device of this version of a video endoscopic probe is made up of a bundle of non-ordered optical fibers 20 whose proximal end is fixedly housed in the longitudinal opening 51 and arranged in the cylindrical piece 50 which is fixedly integral with the proximal lower part of the control handle 3 of the video endoscopic probe. The cylindrical handle 5, whose distal end fixedly surrounds the cylindrical piece 50, is used as a housing for a light fixture 53 which has a reflector calibrated so that the light radiation emitted by the light is concentrated on the proximal side 30, suitably polished, of the proximal end of the bundle of lighting fibers 20. The light fixture 53 is electrically supplied by a regulated electronic power supply 54 which is also housed in the cylindrical handle 5 and whose supply voltage is identical to that of the video processor 9.

The proximal end of the cylindrical handle 5 has a multipin electrical connection coupling 55. This coupling is electrically connected with the proximal end of an internal electrical cable 42 and has a branch circuit 41 which ensures the electrical power supply of the regulated electronic power supply 54 of the light fixture 53. It also has a circuit 40 which ensures the electrical power supply of the video processor 9. The branch circuit 40 runs, for this purpose, through the cylindrical handle 5, the longitudinal opening 52 of the cylindrical piece 50, and through the control handle 3. The multipin electrical connection coupling 55 is also electrically connected with the proximal end of an internal multiconductor electrical cable 35 connecting the coupling to the video processor 9 and running, for this purpose, through the cylindrical handle 5, the longitudinal opening 52 of the cylindrical piece 50, and through the control handle 3. The multiconductor cable ensures the transmission of the video signal generated by the video processor 9 as well as the RS 232T connection of the processor.

There are many applications for a video endoscopic probe with a distal color CCD sensor constituting the present invention can, for example, arise from the technical inspection field as well as from the medical field.

The present invention is in no way limited to the modes of implementation, of execution or of applications which have just been explicitly described. The present invention rather includes all variants which may come to the mind of the technician on the subject without consequently leaving the scope of the present invention.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A video endoscopic probe comprising:
   a distal terminal comprising an objective, a color CCD sensor, and an electrical interface microcircuit;
   a continuous bundle of optical fibers having a proximal end coupled to a light source and a distal end located in said distal terminal;
   a video processor coupled to said electrical interface microcircuit, wherein said video processor is adapted to supply and synchronize electrical signals from said color CCD sensor, to process the electrical signal generated by said color CCD sensor, and to produce a video signal;
   a color video monitor adapted to receive the video signal produced by said video processor;
   a tubular probe coupled to said distal terminal;
   a control handle adapted to include said video processor and said color video monitor;
   said tubular probe comprising a proximal end coupled to said control handle;
   a multiconductor electrical cable coupling said video processor to said electrical interface microcircuit;
   a regulated power supply adapted to deliver stabilized direct current voltages for operating at least said video processor, said video monitor, said electrical interface microcircuit, and said color CCD sensor;
   an electrical cable coupled to said video processor being adapted to supply a direct current electrical voltage to said power supply, wherein said power supply is adapted to output a direct current supply voltage through said electrical cable which is variable around a nominal value;
   a cylindrical piece fixedly coupled to a proximal lower part of said control handle;
   said control handle comprising a hand-held handle having a distal end arranged to fixedly surround said cylindrical piece and a proximal end comprising an interface coupling; and
   said cylindrical piece comprising a first longitudinal opening being adapted to pass said bundle of optical fibers, and a second longitudinal opening being adapted to pass said electrical cable.

2. The video endoscopic probe in accordance with claim 1, wherein said continuous bundle of optical fibers are adapted to illuminate a target,
   wherein said video processor and said color video monitor are integrated in said control handle,
   wherein said color video monitor directly receives the video signal from said video processor,
   wherein said hand-held handle comprises a cylindrical tubular hand-held handle, and
   wherein the nominal voltage is 12 volts and the direct supply voltage varies between approximately 9 and 16 volts.

3. The video endoscopic probe in accordance with claim 1, further comprising an umbilical cable having a distal end coupled to said proximal end of the hand-held handle and having a proximal end coupled to a connection device;
   said connection device comprising an axial terminal in which said proximal end of said bundle of optical fibers are located, wherein said bundle of fibers are adapted to couple said connection device to said distal terminal;
   said axial terminal being plugable into an external light generator;
   said connection device comprising a lateral electrical connection coupling that is electrically coupled to a proximal end of said electrical cable, wherein said electrical cable is adapted to couple said connection device to said video processor;
   said lateral electrical connection coupling being connectable to an external electrical source.

4. The video endoscopic probe in accordance with claim 3, wherein said umbilical cable is a tubular umbilical cable,
   wherein a distal end of said connection device, to which said proximal end of said umbilical cable is coupled, does not include an internal electrical adaptation device, wherein said bundle of optical fibers run directly and without a break of continuity through said umbilical cable, said hand-held handle, said first longitudinal opening, said control handle, and said tubular probe, and wherein said electrical cable runs directly and without a break of continuity through said umbilical cable, said hand-held handle, said second longitudinal opening, and said control handle.

5. The video endoscopic probe in accordance with claim 3, further comprising a multiconductor cable that includes a coaxial cable, wherein said coaxial cable is coupled to said video processor and is adapted to receive the video signal;

said connection device further comprising a lateral coaxial connection coupling that is electrically coupled to said coaxial cable, wherein said coaxial cable is adapted to couple said connection device to said video processor;

said lateral coaxial connection coupling being connectable to an external video monitor.

6. The video endoscopic probe in accordance with claim 5, wherein said multiconductor cable is adapted to run successively through said umbilical cable, said hand-held handle, said second longitudinal opening, and said control handle.

7. The video endoscopic probe in accordance with claim 3, further comprising a digital microcontroller having an RS 232T interface, said digital microcontroller being adapted to control operation of said video processor;

said multiconductor cable comprising a plurality of conductors coupled to an RS 232T coupling, wherein said RS 232T coupling is coupled to said RS 232T interface;

said connection device further comprising a lateral multipin connection coupling which is electrically coupled to said RS 232T link, wherein said RS 232T link is adapted to couple said connection device to said video processor; and said lateral multipin connection coupling being couplable to said RS 232T interface, whereby said RS 232T interface is couplable to said RS 232T link.

8. The video endoscopic probe in accordance with claim 7, wherein said multiconductor cable is adapted to run successively through said umbilical cable, said hand-held handle, said second longitudinal opening, and said control handle.

9. The video endoscopic probe in accordance with claim 1, wherein said proximal end of said bundle of optical fibers is mounted within said first longitudinal opening, and said video endoscopic probe further comprises:

a light fixture located within said hand-held handle, said light fixture comprising a reflector adapted to concentrate light radiation emitted by said light source onto said proximal end of said bundle of optical fibers;

said light fixture being adapted to receive a stabilized voltage from a regulated light fixture power supply, wherein said regulated power supply is located within said hand-held handle, and wherein said power supply voltage to said light fixture is the same as that to the video processor; and said interface coupling comprising a multipin electrical connection coupling that is electrically connected to an internal electrical cable forming a first branch circuit to supply electrical power to said regulated light fixture power supply and a second branch circuit to supply electrical power to said regulated power supply, wherein said second branch circuit is adapted to run successively through said hand-held handle, said second longitudinal opening, and said control handle.

10. The video endoscopic probe in accordance with claim 9, further comprising an internal multiconductor cable;

said multipin electrical connection coupling being adapted to be electrically coupled to said internal multiconductor electrical cable, and said multipin electrical connection comprising an RS 232T link; and said internal multiconductor cable being arranged to couple said multipin electrical connection coupling to said video processor, wherein said internal multiconductor cable is adapted to at least one of transmit the video signal generated by said video processor and couple said RS 232T link to said video processor.

11. The video endoscopic probe in accordance with claim 10, wherein said internal multiconductor cable is adapted to run successively through said hand-held handle, said second longitudinal opening, and said control handle, and wherein said proximal end of said bundle of optical fibers are suitably polished to receive said light radiation.

12. The video endoscopic probe in accordance with claim 1, further comprising:

a digital microcontroller coupled to a panel of operating keys, wherein said digital controller is adapted to control said video processor;

a device for adjusting white balance of the video processor as a function of chromatic characteristics of a video image of the target, which is illuminated by said bundle of optical fibers; and said panel of operating keys comprising has a special key adapted to automatically lock said white balance adjustment device.

13. The video endoscopic probe in accordance with claim 12, wherein said panel of operating keys are located on said control handle.

14. The video endoscopic probe in accordance with claim 1, wherein a sensitivity of said video processor is regulatable as a function of a lighting level of the target through an automatic control mode that simultaneously considers a gain of said video processor and an opening of an electronic diaphragm of said distal color CCD sensor, which automatically compensates for great variations in lighting level occurs.

15. The video endoscopic probe in accordance with claim 1, further comprising a phase shift device adapted to compensate for transmission delays of said electrical signals traveling through said multiconductor electrical cable;

said phase shift device comprising a delay line acting on a pixel clock generated by said video processor and transmitted to said electrical interface circuit.

16. The video endoscopic probe in accordance with claim 15, said phase shift device further comprising a delay line acting on a clock which synchronizes sampling by said video processor of an incident electrical signal generated by said distal color CCD sensor and transmitted by said multiconductor cable.

17. The video endoscopic probe in accordance with claim 1, further comprising a prop device coupled to said tubular probe and to said distal terminal;

said prop device comprising a series of rings, wherein each ring is articulated with its adjacent rings to enable said prop device to be oriented in two perpendicular planes;

two flexible cables, which extend through said tubular probe, being adapted to control translational movements of said prop device in said two perpendicular planes; and an actuator located within said control handle being coupled to said two flexible cables and being adapted to drive said two flexible cables in respective ones of said two perpendicular planes.

18. The video endoscopic probe in accordance with claim 17, wherein said actuator comprises two mechanical actuators, and wherein each of the two mechanical actuators coupled to an external control wheel.

19. The video endoscopic probe in accordance with claim 17, wherein said actuator comprises two motorized actuators.

20. The video endoscopic probe in accordance with claim 19, further comprising a joystick adapted to control a starting and rotational direction of said two motorized actuators, wherein said joystick is coupled to said control handle and is adapted for movement with four degrees of freedom.

21. The video endoscope probe in accordance with claim 19, wherein power supply voltages for said two motorized actuators are the same as the power supply voltage of said video processor.

22. A video endoscopic probe comprising:

a distal terminal comprising an objective, a color CCD sensor, and an electrical interface microcircuit;

a continuous bundle of optical fibers coupled to a light source and to said distal terminal;

a video processor coupled to said electrical interface microcircuit;

a color video monitor adapted to receive the video signal produced by said video processor;

a tubular probe coupled to said distal terminal;

a control handle adapted to include said video processor and said color video monitor;

said tubular probe coupled to said control handle;

a multiconductor electrical cable coupling said video processor to said electrical interface microcircuit;

a regulated power supply adapted to deliver stabilized direct current voltages for operating at least said video processor, said video monitor, said electrical interface microcircuit, and said color CCD sensor;

an electrical cable coupled to said video processor being adapted to supply a direct current electrical voltage to said power supply, wherein said power supply is adapted to output a direct current supply voltage through said electrical cable which is variable around a nominal value;

a cylindrical piece fixedly coupled a lower part of said control handle;

said control handle comprising a hand-held handle having a portion arranged to fixedly surround said cylindrical piece and further having an interface coupling; and said cylindrical piece comprising a first longitudinal opening being adapted to pass said bundle of optical fibers, and a second longitudinal opening being adapted to pass said electrical cable.

* * * * *